United States Patent
Fallah-Araghi et al.

(10) Patent No.: US 10,883,102 B2
(45) Date of Patent: Jan. 5, 2021

(54) DROPLET-BASED SELECTION BY INJECTION

(71) Applicant: Novozymes A/S, Bagsvaerd (DK)

(72) Inventors: Ali Fallah-Araghi, Copenhagen (DK); Ole Skyggebjerg, Valby (DK)

(73) Assignee: NOVOZYMES A/S, Bagsvaerd (DK)

( * ) Notice: Subject to any disclaimer, the term of this patent is extended or adjusted under 35 U.S.C. 154(b) by 93 days.

(21) Appl. No.: 15/560,017

(22) PCT Filed: Mar. 15, 2016

(86) PCT No.: PCT/EP2016/055577
§ 371 (c)(1),
(2) Date: Sep. 20, 2017

(87) PCT Pub. No.: WO2016/150771
PCT Pub. Date: Sep. 29, 2016

(65) Prior Publication Data
US 2018/0094255 A1 Apr. 5, 2018

(30) Foreign Application Priority Data
Mar. 20, 2015 (EP) ..................................... 15160072

(51) Int. Cl.
*C12N 15/10* (2006.01)
*C12Q 1/6806* (2018.01)

(52) U.S. Cl.
CPC ....... *C12N 15/1075* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 2006/0078888 A1* | 4/2006 | Griffiths | B01F 3/0807 435/6.11 |
| 2008/0014589 A1* | 1/2008 | Link | B01F 3/0807 435/287.2 |
| 2010/0022414 A1* | 1/2010 | Link | B01F 3/0807 506/18 |
| 2011/0159511 A1* | 6/2011 | Lenhard | C12Q 1/02 435/6.15 |

FOREIGN PATENT DOCUMENTS

| | | |
|---|---|---|
| WO | 1999002671 A2 | 1/1999 |
| WO | 2003044187 A2 | 5/2003 |
| WO | 2007089541 A2 | 8/2007 |
| WO | 210151776 A1 | 12/2010 |
| WO | 2012156744 A2 | 11/2012 |

OTHER PUBLICATIONS

Chen et al, 2013, Nano Micro Lett 5(1), 66-80.

* cited by examiner

*Primary Examiner* — Tracy Vivlemore
*Assistant Examiner* — Sahana S Kaup
(74) *Attorney, Agent, or Firm* — David A. Fazzolare

(57) ABSTRACT

A method for the identification of a polynucleotide encoding an enzyme of interest in a microfluidic device by providing an emulsion of microfluidic droplets comprising a library of polynucleotides encoding one or more enzyme, introducing a concentrated PCR solution which allows PCR amplification of the polynucleotides into selected droplets and/or introducing a lethal solution into deselected droplets, and identifying a polynucleotide encoding an enzyme of interest.

12 Claims, No Drawings

DROPLET-BASED SELECTION BY INJECTION

CROSS-REFERENCE TO RELATED APPLICATIONS

This application is a 35 U.S.C. 371 national application of PCT/EP2016/055577, filed Mar. 15, 2016, which claims priority or the benefit under 35 U.S.C. 119 of European application no. 15160072.3, filed Mar. 20, 2015. The contents of these applications are fully incorporated herein by reference.

FIELD OF THE INVENTION

The present invention relates to a microfluidic or "lab-on-a-chip" method. More specifically, it relates to how to use fluid-injection as a means for selecting or deselecting droplets of water in an immiscible carrier fluid. The water droplets are sometimes referred to as microdroplets or microencapsulations, they typically have an average diameter of about 20 micrometer and are used as compartments or miniscule reaction vessels. They can contain live microbial cells that are, for example, secreting an enzyme. The droplets may also contain other components, for example, a fluorogenic enzyme substrate that can reveal the activity of an enzyme produced by a microbial cell within a droplet.

BACKGROUND OF THE INVENTION

The general concept of isolating one or more genetic elements encoding a gene product having a desired activity, comprising of the steps of: (a) compartmentalising genetic elements into microcapsules; (b) expressing the genetic elements to produce their respective gene products within the microcapsules; (c) sorting the genetic elements which produce the gene product having a desired activity was described already in 1999 (WO 99/02671).

It has been described to use in vitro expression systems in microcapsules along with an emulsion-stabilizing chemically inert silicone-based surfactant (WO 03/044187).

Manipulation of microdroplets, including merger or coalescence of several droplets has been achieved, for example, through the application of an electric field (WO 2007/089541).

A number of comprehensive reviews are available and many of the microfluidic components are commercially available. The field of microfluidics is in rapid development and any potential improvements are highly desired.

SUMMARY OF THE INVENTION

The inventors of the instant methods have shown that identification of a polynucleotide encoding an enzyme of interest can be done very effectively in a microfluidic device by providing an emulsion of microfluidic droplets comprising a library of polynucleotides encoding one or more enzyme, introducing a concentrated PCR solution which allows PCR amplification of the polynucleotides into selected droplets and/or introducing a lethal solution into deselected droplets, and then identifying a polynucleotide encoding an enzyme of interest.

Accordingly, the present invention provides methods for the identification of a polynucleotide encoding an enzyme of interest in a microfluidic device, said method comprising the steps of:

a) providing an emulsion of microfluidic droplets comprising a library of polynucleotides encoding one or more enzyme, wherein each droplet comprises at most a single member of the library, and expressing the library of polynucleotides to produce the one or more enzyme;

b) introducing an aliquot comprising a substrate for the one or more enzyme into each droplet, wherein the presence of one or more active enzyme of interest will convert the substrate into a screenable product;

c) determining positive droplets that contain the screenable product above a predetermined threshold level which, in turn, also determines the negative droplets;

d) introducing an aliquot of concentrated PCR solution comprising nucleotides, a suitable DNA polymerase and a set of PCR primers which allows PCR amplification of the polynucleotides encoding the one or more enzyme of interest into each positive droplets determined in step (c); and/or introducing an aliquot of a solution which results in DNA denaturation as well as enzyme denaturation and/or cell lysis into the negative droplets determined in step (c);

e) cloning or PCR amplifying the polynucleotide encoding the one or more enzyme of interest from the positive droplets; and f) identifying a polynucleotide encoding an enzyme of interest from the cloned or PCR amplified polynucleotides in step (e).

Definitions

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

DETAILED DESCRIPTION OF THE INVENTION

In a first aspect, the invention relates to methods for the identification of a polynucleotide encoding an enzyme of interest in a microfluidic device, said method comprising the steps of:

a) providing an emulsion of microfluidic droplets comprising a library of polynucleotides encoding one or more enzyme, wherein each droplet comprises at most a single member of the library, and expressing the library of polynucleotides to produce the one or more enzyme;

b) introducing an aliquot comprising a substrate for the one or more enzyme into each droplet, wherein the presence of one or more active enzyme of interest will convert the substrate into a screenable product;

c) determining positive droplets that contain the screenable product above a predetermined threshold level which, in turn, also determines the negative droplets;

d) introducing an aliquot of concentrated PCR solution comprising nucleotides, a suitable DNA polymerase and a set of PCR primers which allows PCR amplification of the polynucleotides encoding the one or more enzyme of interest into each positive droplets determined in step (c); and/or introducing an aliquot of a solution which results in DNA denaturation as well as enzyme denaturation and/or cell lysis into the negative droplets determined in step (c);

e) cloning or PCR amplifying the polynucleotide encoding the one or more enzyme of interest from the positive droplets; and f) identifying a polynucleotide encoding an enzyme of interest from the cloned or PCR amplified polynucleotides in step (e).

In a preferred embodiment of the invention, the enzyme of interest is a hydrolase, isomerase, ligase, lyase, oxidoreductase, or transferase; preferably the enzyme of interest is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

In yet another preferred embodiment, the library encodes one or more hydrolase, isomerase, ligase, lyase, oxidoreductase, or transferase; preferably the library encodes one or more alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In one preferred embodiment, the library encodes different variants of the same enzyme and in another, the library comprises two or more different polynucleotides encoding the same enzyme.

It is envisioned that the method of the present invention may employ a library of isolated polynucleotides and in vitro expression systems. However, a preferred embodiment of the invention is an in vivo setup, wherein the library is comprised within a prokaryotic host cell; preferably within a Gram-positive host cell; more preferably within a *Bacillus* host cell; even more preferably within a *Bacillus alkalophilus, Bacillus amyloliquefaciens, Bacillus brevis, Bacillus*

*circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* host cell; and most preferably within a *Bacillus licheniformis* host cell.

Naturally, each individual polynucleotide of the library is in its own separate host cell. Accordingly, in a preferred embodiment, each droplet in step (a) of the first aspect comprises at most a single host cell.

The activity of the one or more enzyme encoded by the polynucleotide library is assayed either qualitatively or quantitatively by detecting the conversion of an enzyme substrate into a detectable or quantifiable enzyme product. Typically, a fluorogenic enzyme substrate is added which is turned into a fluorescent enzyme product to be detected or measured.

Accordingly, in a preferred embodiment of the invention, the substrate for the one or more enzyme is fluorogenic and the activity of the enzyme converts the fluorogenic substrate into a fluorescent product.

Once a particularly interesting enzyme activity has been detected in a selected droplet, the polynucleotide library member inside the droplet needs to be identified. Typically, the polynucleotide is identified through DNA sequencing.

The polynucleotide may also have been outfitted with an identifying sequence tag to serve as a "bar code" when the library was constructed, thus obviating the need for sequencing. Based on the identification of the bar-code, the DNA sequence of the polynucleotide would then immediately be known and it would, thus, be identified.

In a preferred aspect of the invention, the polynucleotide encoding an enzyme of interest is identified in step (f) by DNA sequencing of the polynucleotide.

In the first aspect of the invention, several aliquotes of solutions are introduced into the droplets. The aliquotes are usually much smaller in volume than the droplets, but they may in principle range in size up to the same volume as the droplets or even larger. In the examples below, the aliquotes are significantly smaller than the droplets. There are many ways of introducing an aliquote into a droplet in a microfluidic device or, termed in another way, to merge or coalesce two droplets.

The design of microfluidic devices that enable the application of an electric field to merge or coalesce two or more droplets is disclosed, for example, in WO 2007/061448. Another way to introduce small aliquotes of an aqueous liquid into an aqueous droplet in a microfluidic device is known as "pico-injection" and is disclosed, for example, in WO 2010/151776.

In the examples below, the aliquotes were introduced into the droplets by merging or coalescing the aliquotes and the droplets through the application of an electric field.

Accordingly, in a preferred embodiment of the first aspect, the aliquotes are introduced into the droplets by merging or coalescing the aliquotes and the droplets through the application of an electric field or by injection.

Polynucleotides

The present invention also relates to a library of polynucleotides encoding one or more enzyme polypeptide, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Applications*, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. Other examples of regulatory sequences are those that allow for gene amplification.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci.* USA 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

Methods of Production

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

EXAMPLES

Example 1

Microfluidic Devices

Microfluidic devices were fabricated by patterning channels into poly(dimethylsiloxane) (PDMS) using soft lithography (Duffy, D.; McDonald, J.; Schueller, O.; Whitesides, G. Anal. Chem. 1998, 70, 4974-4984). Briefly, a mold of SU-8 photoresist (MicroChem Corp., Newton, Mass.) was fabricated on a silicon wafer (SILTRONIX, Archamp, France) by UV exposure (MJB3 contact mask aligner; SUSS MicroTec, Garching, Germany) through a photolithography mask (Selba SA, Versoix, Switzerland) and subsequent development (SU-8 developer; MicroChem Corp.). Curing agent was added to PDMS base (SYLGARD® 184 silicone elastomer kit; Dow Corning Corp., Lyon, France) to a final concentration of 10% (v/v), mixed, and poured over the mold to a depth of 5 mm. Following cross-linking at 65° C. for approx. 12 h, the PDMS was peeled off the mold, and the input and output ports were punched with a 0.75-mm-diameter HARRIS UNI-CORE™ biopsy punch (Electron Microscopy Sciences, Hatfield, Pa.). Particles of PDMS were cleared from the ports using pressurized nitrogen gas. The structured side of the PDMS slab was bonded to a 76×26×1 mm glass microscope slide (Paul Marienfeld GmbH & Co. KG, Lauda-Königshofen, Germany) by exposing both parts to an oxygen plasma (PLASMA PREP™ II plasma oven; GaLa Instrumente GmbH, Bad Schwalbach, Germany) and pressing them together. Finally, the devices were coated with a commercial hydrophobic surface coating agent (AQUAPEL®, Pittsburgh Glassworks Industries, Pittsburgh, Pa.) and subsequently flushed with N2. Liquids were pumped into microfluidic devices using standard pressure infuse/withdraw PHD 22/2000 syringe pumps (Cetoni, Nemesis, Germany).

Example 2

Formation of Emulsions

Emulsions may be produced from many suitable combinations of immiscible liquids. The emulsion of the present invention has an aqueous phase (water containing the biochemical and biological components) present in the form of finely divided droplets and a commercially available hydrophobic, immiscible liquid (HFE-7500 fluorinated oil containing 2% (w/w) PICO-SURF™ surfactant (Sphere Fluidics, Cambridge, UK)) as the carrier fluid in which the droplets are suspended. Such emulsions are termed water in oil (W/O). The emulsion is stabilized by the presence of the surfactant.

The creation of an emulsion requires the application of mechanical energy to force the two phases together. There are a variety of ways of doing this that employ different mechanical devices. We have used a microfluidic device or chip termed a droplet generator that forces the two phases through a fine nozzle, thereby creating monodispersed droplets of water in oil. Such generators are capable of creating a great number of droplets within a very short time, the rate is measured in the kHz range.

Droplets were formed containing Luria Bertani (LB) growth medium with chloramphenicol supplemented with a solution of *Bacillus subtilis* cells expressing a gene library encoding a number of amylase enzyme variants. The cells were diluted so that, statistically, no more than one *Bacillus subtilis* cell would be encapsulated into each droplet according to a Poisson distribution. The concentration of cells used in this experiment allowed only about 34% on the droplets to be occupied by a (single) bacterium, leaving close to 66% of the droplets in the emulsion empty of any living cell(s).

The total aqueous phase (with a low concentration of bacterial cells) was loaded into PTFE tubing (0.56×1.07 mm internal/external diameter, Fisher Bioblock Scientific) and the tubing was connected to a syringe. The aqueous phase was injected into the droplet generator microfluidic device using a syringe pump at a flow rate of 100 µL/h. Droplets were generated by flow focusing of the resulting stream with the above-mentioned carrier fluid at a flow rate of 250 µL/h. The rate of droplet production was 5 kHz. A library of about 200.000 bacteria was thus encapsulated to provide about 600.000 droplets which statistically contained at most one single cell per droplet (with most of the droplets being empty). The resulting emulsion was stored in a syringe at 37° C. for 8 hours to allow bacterial growth and to allow amylase production and secretion within the droplets.

Example 3

Injection of Amylase Substrate to Detect Enzymatic Activity

After overnight incubation of the emulsion, it was reinjected into another microfluidic device at a rate of 20 µL/h, the droplets being spaced with carrier fluid injected at 120 µL/h. To each of the droplets was added a small volume (about 20% of the droplet volume) of a commercially available fluorogenic amylase substrate (ENZCHEK™ amylase assay kit E33651, Life Technologies). The addition of substrate to the droplets was done by injecting/fusing a continuous substrate phase into the droplets by electrocoalescence to achieve a final concentration in each droplet of about 25 µg/L of substrate in PBS buffer at a pH of 7. The fusing of droplets with the substrate phase was performed for 30 minutes at a rate of approx. 2,000 fusion events per second by applying an electric field of 600 Volts AC at 30 kHz across electrodes using a Model 623b high voltage amplifier (Trek, Inc.; BF: OPTILAS SAS, Cambridge, UK). The 200.000 original cells in the 600.000 droplets were each provided with the substrate and all the droplets were again collected in a syringe and then incubated for 30 min at room temperature to allow the amylase enzyme to react with the substrate in the droplets.

Example 4

Selection of Amylase Variants by Cell Lysis

After incubation of the droplets, the emulsion was reinjected into another microfluidic device at 20 µL/h and spaced with carrier fluid at 120 µL/h. The fluorescence of all 600.000 droplets was measured with a photomultiplier tube (PMT) as they passed through a 488 nm excitatory wavelength laser beam. Droplets that did not display a fluorescent signal, thus indicating either no living cells in the droplet or only cells secreting inactive amylase variants, were injected with a lethal KOH/EDTA solution using the same electrocoalescence approach as outlined above. The electric field was switched on and off depending on the fluorescent signal detected from each droplet. A solution of 400 mM KOH and 10 mM EDTA was injected into these negative droplets to achieve a final concentration of 200 mM of KOH and 5 mM EDTA. The injected KOH rapidly mixed within the negative droplets and immediately lysed any cells therein as well as denatured any protein or nucleic acids, thereby rendering the content of the negative droplets ready to be discarded. Positive droplets that displayed a fluorescent signal, on the other hand, were not injected with the lethal solution. The positive could also have been physically sorted and seperated from the negative droplets and then collected but, in this example, we simply deselected the negative droplets by lethal injection.

After deselection, we broke the emulsion by adding 10 µL of PICO-BREAK™ (Sphere Fluidics, Cambridge, UK) and 10 mL of fresh growth media. The remaining *Bacillus* cells originating from the positive droplets were not affected by the KOH and EDTA from the deselected droplets, because after all droplets were coalesced the KOH/EDTA concentrations were diluted a million-fold. The resulting solution was incubated overnight with shaking at 220 rpm (Innova 400, Fisher scientist) at 37° C. to allow bacterial growth.

Example 5

Selection by PCR

As an alternative selection principle, we also carried out direct PCR in the positive droplets as follows: The procedures of Examples 2-3 were repeated but after the final incubation of the droplets in Example 3, the emulsion was reinjected into a new microfluidic device at 20 µL/h and spaced with HFE-7500 fluorinated oil containing 2% w/w PICO-SURF® surfactant (Sphere fluidics, Cambridge) at 120 µL/h. The fluorescence of each droplet was measured with a photomultiplier tube (PMT) as it passed through a 488 nm laser spot. Each positive droplet that displayed a fluorescent signal above a certain pre-set background level was injected with a PCR solution. We used a continuous phase containing a 10-fold concentrated PCR reaction solution using KAPA HiFi HotStart ReadyMix PCR kit (KK2606, Life technologies) and primers specific for the amplification of the amylase gene, each at 3 µM concentration. Each positive droplet was infused with the continuous PCR phase using an electric field. Afterwards each droplet contained a final concentration of 300 nM of the primers specific for the amplification of the amylase-encoding gene and 1-fold PCR mix. Negative droplets that did not display the required fluorescent signal were not injected with the PCR solution. The injection of the continuous phase PCR solution was done through the activation of a pulse of high-voltage alternating current (AC) 1000V applied across the electrodes adjacent to the continuous aqueous phase. The electric field was switched on and off depending on the fluorescent signal detected from each droplet.

After the selection the emulsion was recovered and placed in a thermocycler to perform PCR on the emulsion. The PCR reactions were done for 3 min at 95° C. followed by 30 cycles at 98° C., 20 s; 65° C., 20 s; and 72° C., 1.5 min, and a final incubation step of 5 min at 72° C.

After thermocycling, the emulsion was broken and the droplets were coalesced by adding 10 µL of PICO-BREAK® (Spherefluidics, Cambridge, UK). The aqueous phase was recovered through phase separation between the aqueous phase and the oil phase. Only the droplets that displayed a fluorescent signal and were injected with the PCR mix along with primers have had their amylase-encoding genes amplified.

The sequences of the positive hits can be identified by any suitable standard methods, for example, by cloning and sequencing the genes or by sequencing the genes directly in a so-called "NextGeneration" sequencing setup using systematically labelled sequencing primers as disclosed in, e.g. WO 2012/019765.

It may be advantageous to employ biotin-labelled primers in the PCR solution. This would allow a quick and easy recovery of the amplified PCR products using, e.g., a chromatography column with streptavidin.

Example 6

Microfluidic Setups

Microfluidic devices comprising more than one injector on the same device may be employed, so that droplets of interest can be fused with a number of different fluids rapidly. This would allow sorting of droplets with a positive signal into a different number of bins, for example, determined by the intensity or their fluorescent return signal, i.e., the enzymatic activity. This may be done by injecting the droplets with different PCR mixes containing different primers. Each bin may be defined by a specific fluorescence intensity range. This would allow selection of the droplets based on different thresholds. The choice of the bin would depend on the level of fluorescent signal coming from the droplet. Each set of primers in each injector may have a unique tag-sequence identifying the same number of bins as there are injectors. For example a device with three injectors would allow sorting the emulsion in three fractions. In this way each fraction could be injected with a different set of tagged primers to indicate the level of enzymatic activity (the phenotype) in the host cell of origin.

The invention claimed is:

1. A method for the identification of a polynucleotide encoding an enzyme of interest in a microfluidic device, said method comprising the steps of:
   a) providing an emulsion of microfluidic droplets comprising a library of polynucleotides encoding one or more enzyme, wherein each droplet comprises at most a single member of the library comprised within a single prokaryotic host cell, and expressing the library of polynucleotides to produce the one or more enzyme;
   b) introducing an aliquot comprising a substrate for the one or more enzyme into each droplet, wherein the presence of one or more active enzyme of interest will convert the substrate into a screenable product;
c) determining positive droplets that contain the screenable product above a predetermined threshold level which, in turn, also determines the negative droplets;
d) introducing an aliquot of concentrated PCR solution comprising nucleotides, a suitable DNA polymerase and a set of PCR primers which allows PCR amplification of the polynucleotides encoding the one or more enzyme of interest into each positive droplets determined in step (c); and/of introducing an aliquot of a solution which results in DNA denaturation as well as enzyme denaturation and/or cell lysis into the negative droplets determined in step (c);
e) cloning or PCR amplifying the polynucleotide encoding the one or more enzyme of interest from the positive droplets; and
f) identifying a polynucleotide encoding an enzyme of interest from the cloned or PCR amplified polynucleotides in step (e).

2. The method of claim 1, wherein the enzyme of interest is a hydrolase, isomerase, ligase, lyase, oxidoreductase, or transferase.

3. The method claim 1, wherein the library encodes a hydrolase, isomerase, ligase, lyase, oxidoreductase, or transferase.

4. The method of claim 1, wherein the library encodes different variants of the same enzyme.

5. The method of claim 1, wherein the library comprises two or more different polynucleotides encoding the same enzyme.

6. The method of claim 1, wherein the substrate for the one or more enzyme is fluorogenic and wherein the activity of the enzyme converts the fluorogenic substrate into a fluorescent product.

7. The method of claim 1, wherein the polynucleotide encoding an enzyme of interest is identified in step (f) by DNA sequencing of the polynucleotide.

8. The method of claim 1, wherein the aliquots are introduced into the droplets by merging or coalescing the aliquots and the droplets through the application of an electric field or by injection.

9. The method of claim 2, wherein the enzyme of interest is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucanotransferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

10. The method of claim 3, wherein the library encodes an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

11. The method of claim 1, wherein the prokaryotic host cell is a *Bacillus* host cell.

12. The method of claim 11, wherein the *Bacillus* host cell is selected from the group consisting of a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* host cell.

* * * * *